United States Patent
Sans

(10) Patent No.: US 11,633,373 B2
(45) Date of Patent: Apr. 25, 2023

(54) METHOD FOR REDUCTION OF BEHAVIORAL DISORDERS IN PIGS

(71) Applicant: Alzchem Trostberg GmbH, Trostberg (DE)

(72) Inventor: Jürgen Sans, Trostberg (DE)

(73) Assignee: Alzchem Trostberg GmbH, Trostberg (DE)

( * ) Notice: Subject to any disclaimer, the term of this patent is extended or adjusted under 35 U.S.C. 154(b) by 0 days.

(21) Appl. No.: 17/758,317

(22) PCT Filed: Feb. 24, 2021

(86) PCT No.: PCT/EP2021/054580
§ 371 (c)(1),
(2) Date: Jul. 1, 2022

(87) PCT Pub. No.: WO2021/175677
PCT Pub. Date: Sep. 10, 2021

(65) Prior Publication Data
US 2023/0025539 A1 Jan. 26, 2023

(30) Foreign Application Priority Data

Mar. 4, 2020 (DE) .................... 10 2020 105 769.5

(51) Int. Cl.
*A61K 31/198* (2006.01)
*A23K 50/30* (2016.01)
*A23K 20/105* (2016.01)
*A61P 25/00* (2006.01)

(52) U.S. Cl.
CPC .......... *A61K 31/198* (2013.01); *A23K 20/105* (2016.05); *A23K 50/30* (2016.05); *A61P 25/00* (2018.01)

(58) Field of Classification Search
CPC .... A61K 31/198; A23K 20/105; A23K 50/30; A61P 25/00
See application file for complete search history.

(56) References Cited

U.S. PATENT DOCUMENTS 8,501,810 B2 * 8/2013 Gastner .................... A61P 3/02
514/565
2007/0231370 A1 10/2007 Gastner et al.

FOREIGN PATENT DOCUMENTS

| CN | 103859208 A | 6/2014 |
| CN | 105076769 A | 11/2015 |
| WO | 2005120246 A1 | 12/2005 |

OTHER PUBLICATIONS

"The Risks Associated with Tail Biting in Pigs and Possible Means to Reduce the Need for Tail Docking Considering the Different Housing and Husbandry Systems—Scientific Opinion of the Panel on Animal Health and Welfare", European Food Safety Authority, retrieved from https://efsa.onlinelibrary.wiley.com/doi/epdf/10.2903/j.efsa.2007.611, EFSA Journal, Dec. 20, 2007, 109 pages.
Hunter et al., "The Relationship Between Tail Biting in Pigs, Docking Procedure and Other Management Practices", The Veterinary Journal, vol. 161, No. 1, Jan. 2001, pp. 72-79.
Moinard et al., "A Case Control Study of On-Farm Risk Factors for Tail Biting in Pigs", Applied Animal Behaviour Science, vol. 81, No. 4, May 21, 2003, pp. 333-355.
International Application No. PCT/EP2021/054580, "International Search Report and Written Opinion (Partial translation)", dated May 14, 2021, 18 pages.
Quanz "Healthy tail through feed additives?", retrieved from https://www.bwagrar.de/Aktuelles/Gesunder-Schwanz-durch-Futterzusatzstoffe,QUIEPTU5NDUwMDkmTUIEPTUxNjQ0.html, BWagrar, Oct. 22, 2018, pp. 1-3.
Sambraus, "Mouth-Based Anomalous Syndromes", Ethology of Farm Animals, Chapter 31, 1985, pp. 391-422.

* cited by examiner

*Primary Examiner* — Sahar Javanmard
(74) *Attorney, Agent, or Firm* — Kilpatrick Townsend & Stockton LLP

(57) ABSTRACT

The present invention relates to the use of guanidinoacetic acid and a method of treating caudophagia in pigs.

9 Claims, 3 Drawing Sheets

| 12 m², no GAA | 12 m², 0.04 % GAA | 12 m², 0.12 % GAA |
|---|---|---|
| 14.4 m², no GAA | 14.4 m², 0.04 % GAA | 14.4 m², 0.12 % GAA |
| 24 m², no GAA | 24 m², 0.04 % GAA | 24 m², 0.12 % GAA |
| 36 m², no GAA | 36 m², 0.04 % GAA | 36 m², 0.12 % GAA |

Figure 1

| 12 m², 0.04 % GAA | 12 m², no GAA | 12 m², 0.12 % GAA |
| --- | --- | --- |
| 14.4 m², 0.04 % GAA | 14.4 m², no GAA | 14.4 m², 0.12 % GAA |
| 24 m², 0.04 % GAA | 24 m², no GAA | 24 m², 0.12 % GAA |
| 36 m², 0.04 % GAA | 36 m², no GAA | 36 m², 0.12 % GAA |

Figure 2

| | | |
|---|---|---|
| 12 m², 0.04 % GAA | 12 m², 0.12 % GAA | 12 m², no GAA |
| 14.4 m², 0.04 % GAA | 14.4 m², 0.12 % GAA | 14.4 m², no GAA |
| 24 m², 0.04 % GAA | 24 m², 0.12 % GAA | 24 m², no GAA |
| 36 m², 0.04 % GAA | 36 m², 0.12 % GAA | 36 m², no GAA |

Figure 3

METHOD FOR REDUCTION OF BEHAVIORAL DISORDERS IN PIGS

CROSS REFERENCE TO RELATED APPLICATIONS

This application is a U.S. national phase of International Patent Application No. PCT/EP2021/054580 filed on Feb. 24, 2021, which claims priority to German Patent Application No. 10 2020 105 769.5, filed in Germany on Mar. 4, 2020. The entire contents of both applications are hereby incorporated herein by this reference.

The present invention relates to the use of guanidinoacetic acid and a method of treating caudophagia in pigs.

The domestic pig (lat. Sus scrofa domesticus, hereafter simply called pig) is the domesticated form of the wild boar and forms a single species with it. It therefore belongs to the family of the real pigs. The pig is one of the oldest domesticated domestic animals in the history of human civilization and has been kept for meat production for probably 9000 years. In Europe and other regions of the world, pork is one of the most commonly eaten meats.

A common behavioral disorder in pigs during their breeding and fattening is tail biting, scientifically also called caudophagia. This behavioral disorder has a great economic importance [see The EFSA Journal (2007) 611, 1-13: The risks associate with tail biting in pigs and possible means to reduce the need for tail docking considering the different housing and husbandry systems]. The phenomenon of behavioral disorders includes tail biting as well as injuries to ears, flanks or limbs.

Through centuries of breeding, the pigs became more agile, but also more sensitive and susceptible to environmental influences. Furthermore, the strawless slatted floor was introduced. Both factors intensified the problem of tail biting [cf. Sambraus, H. (1985): Mouth-based anomalous syndromes, In: Ethology of arm animals. Worldanimal science A5. A. F. Fraser: Elsevier 1985, 391-421].

Revenue losses may result from reduced weight gain (fattening performance). Discarding of the carcass may also be necessary due to infections. In general, tail biting leads to a reduction in animal welfare.

As a possible preventive measure to avoid tail biting, the tails of piglets are docked, thus reducing health damage (such as tail necrosis) in the piglet breeding and fattening phase. Docking represents the safest method to prevent tail biting [Moinard, C.; Mendel, M.; Nicol, C.; Green, L. (2003): A case control study of on-farm risk factors for tail biting in pigs. Applied Animal Behaviour Science 81(4), 333-355], [Hunter, E; Jones, T.; Guise, H.; Penny, R.; Hoste, S. (2001): The relationship between tail biting in pigs, docking procedure and other management practices. The Veterinary Journal 161, 72-79].

However, for animal welfare reasons, this measure should only be carried out in exceptional cases. According to an EU Guideline 2008/120/EC laying down minimum standards for the protection of pigs, routine docking of piglets' tails is prohibited. Nevertheless, a high number of piglets are docked in Germany. The farms have a certificate from the supervising veterinarian confirming the indispensability of tail docking [cf. Knoop, S.; Schrade, H. (2010): Problematic tail biting/docking in pigs. Bildungs- and Wissenszentrum Boxberg, Landesanstalt für Schweinezucht].

Various measures should be able to minimize tail biting in pigs. A behavioral recommendation has been published for this purpose [cf. Meyer, E. (2019): checklist for the prevention of behavioral disorders, URL: [https://www.tsk-sachsen.de/index.php/tiergesundheitsdienste/schweinegesundheit/veroeffent lichungenschweine/232-ueberarbeitete-checkliste-zur-vermeidung-von-verhaltensstoerungen].

Named measures for housing conditions are the separation of problem animals, housing density, sorting, light design, pen structure. Further measures are aimed at the housing climate, feed and water, activity and animal health.

The disadvantage of this method is, however, that although the animal-animal contacts are reduced by a low housing density, the production rate per $m^2$ decreases simultaneously. Furthermore, the recommended measures listed are very expensive to implement on a daily basis and require considerable investment.

Tail inflammation and necrosis must be avoided to maintain an intact curly tail. Endotoxins may be responsible for the inflammatory processes. These toxins primarily originate from the intestine. Mycotoxins (of fungal origin) can affect degradation of endotoxins, as mycotoxins weaken the intestinal barrier and negatively affect the immune system and metabolism [see Quanz, G. (22 Oct. 2018) Press release LWZ Eichhoff: Healthy tail through feed additives?, URL: [https://www.bwagrar.de/Aktuelles/Gesunder-Schwanz-durch-Futterzusatzstoffe, QUIEPTU5NDUwMDkmTUIEPTUxNjQ0.html].

In order to render the endotoxins and mycotoxins harmless, a wide variety of preparations are offered by the manufacturers of veterinary medicines. However, these preparations usually have side effects that are undesirable for the fattening farms.

Tail biting can occur in all phases of life, increasingly in conventionally, but also in organically managed farms [cf. Goβmann, J.; Hoy, S. (2014): Graspellets kontra Schwanzbeiβen, dlz primus schwein 10/2015, 42-45]. It was found that animals fed 5% meadow grass pellets in addition to their standard feed ration were 11% and 13% less prone to tail biting, respectively. Tail biting is accompanied by diarrhea in the animals. A reduction in tail biting thus also reduces diarrhea. A disadvantage of the method described is that relatively modest success was achieved by adding relatively large amounts of grass pellets.

Furthermore, tail biting is only a phenomenon of a behavioral disorder. By docking the tails, the aggressiveness/behavioral disorder of the animals does not disappear. It only takes away a possibility for the animals to act out their aggressiveness. Therefore, as mentioned above, the aggression will be directed to other body parts such as ears, flanks or the limbs.

Therefore, there is a need for an easy-to-implement and cost-effective method to reduce behavioral problems and associated aggressive behavior in pigs.

This task is solved by the administration of guanidinoacetic acid. Thus, according to a first embodiment, the use of guanidinoacetic acid, in particular the non-therapeutic use of guanidinoacetic acid as an agent for reducing the aggressiveness of pigs, in particular as a non-therapeutic agent for reducing the aggressiveness of pigs, and/or as an agent for treating caudophagia in pigs, in particular as a non-therapeutic agent for treating caudophagia in pigs, is subject matter of the present invention.

According to a further embodiment, a non-therapeutic method for treating caudophagia in pigs is also subject matter of the invention by administering guanidinoacetic acid to the pigs as an agent for reducing aggressiveness, in particular as a non-therapeutic agent for reducing aggressiveness.

Surprisingly, guanidinoacetic acid has been shown to reduce aggressiveness in pigs. Quite surprisingly, it has been shown that pigs show much more peaceful behavior among themselves when given guanidinoacetic acid orally. In basic research, pigs given guanidinoacetic acid have been shown to have fewer biting attacks on conspecifics living with them compared to an untreated control group. The pigs treated in this way showed less behavioral abnormalities in the form of tail biting (caudophagia) compared to the untreated control group. Thus, guanidinoacetic acid can be efficiently used for the treatment and prophylactic management of caudophagia in pigs.

Guanidinoacetic acid (syn. glycocyamine, N-guanylglycine, N-amidinoglycine; $C_3H_7N_3O_2$; CAS No. 352-97-6, hereinafter also referred to as GAA) according to the present invention means the compound per se as a solid, the compound dissolved in a suitable solvent, in particular in water, as well as its salts and here in particular the Na, K, Mg and Ca salt. Guanidinoacetic acid has been available on the market for some time as a feed additive and is approved for use in poultry fattening. Various studies have shown that guanidinoacetic acid improves feed intake and increases fattening performance in poultry.

"Tail biting" is a behavioral disorder of individual pigs biting the curly tails of their group members. This behavioral disorder is also known as caudophagia in professional circles. The cause has not yet been fully clarified by science. However, it is largely certain that it is a multifactorial happening. Triggers of this behavior are usually different factors at the same time. In particular, the climate in the barn, i.e. the temperature, temperature fluctuations, noxious gases and humidity, the housing conditions, i.e. the stocking density, the pen structure, the absolute size of a herd, the feeding places per animal, the feeding technique, feed quantity and feed composition, as well as the general animal health of the pigs and a lack of occupational material can be considered as triggers or causes for this behavioral disorder.

According to the present invention, a treatment is to be understood as both the treatment of an acute abnormality and a prophylactic treatment.

Pigs are naturally sociable animals that live together in more or less large groups. Aggressive behavior among animals can also be observed in nature. However, if pigs are kept in stables, conspicuous behaviors such as aggressiveness increase.

With the investigations underlying the invention, it has now been shown that guanidinoacetic acid can be used in a very effective manner during breeding and fattening of pigs. In particular, in the housing of pigs, guanidinoacetic acid can be used as an agent, in particular as a non-therapeutic agent, for reducing the aggressiveness of pigs, and/or as an agent, in particular as a non-therapeutic agent, for treating caudophagia in pigs. The reduction in aggressiveness is manifested, among other things, in the form of fewer biting attacks into the flanks or other body parts, such as the ears, of conspecifics living together with them.

Thus, in particular, the use, in particular the non-therapeutic use, of guanidinoacetic acid, as well as a non-therapeutic method for the treatment of caudophagia in pigs, is also subject matter of the present invention, in which guanidinoacetic acid is administered as an agent, in particular as a non-therapeutic agent during breeding or fattening of the pigs.

Behavioral disorders in the form of increased aggressiveness and in particular tail biting are less common in piglets or young pigs up to 40 days of age. These behavioral disorders are often observed to increase from 60 days of age. A targeted administration of guanidinoacetic acid in accordance with the present invention from the 90th day of life of the pigs could bring about a significant reduction in aggressiveness and the associated injuries in the subsequent period compared with untreated control groups. Finally, preventive treatment of the pigs with anti-inflammatory drugs or disinfectants could thus also be reduced.

Thus, it is also subject matter of the present invention to provide a use or method by which the non-therapeutic agent is administered from the 60th day of life, in particular from the 70th day of life, preferably from the 80th day of life and most preferably from the 90th day of life of the pigs.

Behavioral disorders in the form of increased aggressiveness and in particular tail biting occur in both conventional and organic livestock farming. Increased space, for example in the form of free range, can prevent these behavioral disorders, but cannot completely eliminate them. On the other hand, these behavioral disorders occur more frequently in livestock housing. The investigations on which the invention is based showed that the administration of guanidinoacetic acid to pigs given a space of 0.75 to 2.25 $m^2$/animal resulted in a sometimes very significant reduction in their aggressiveness towards conspecifics as well as a significant reduction in tail biting. Thus, the administration of guanidinoacetic acid (0.12 wt. %) to animals with a space of 0.9 $m^2$/animal resulted in a reduction of injured animals to almost half. Furthermore, the administration of guanidinoacetic acid (0.12 wt. %) to animals with an available space of 1.5 $m^2$/animal resulted in a reduction of injured animals to more than half (see examples, Table 8).

Thus, it is also subject matter of the present invention to provide a use or method in which the non-therapeutic agent is administered during breeding or fattening of the pigs, wherein the pigs are provided space in the range of 0.75 to 2.25 $m^2$/animal, particularly 0.75 to 1.5 $m^2$/animal, more preferably 0.9 to 1.5 $m^2$/animal.

In any case, the administration of guanidinoacetic acid as an agent, in particular as a non-therapeutic agent, is performed orally according to the present invention. In this regard, the agent may be administered as a single dose or together with a feed for the pigs.

Wheat, barley, triticale, soybean extraction meal, rapeseed extraction meal and grain maize is preferred feed. However, other types of feed such as corn silage, field beans, peas, bran, dried pulp, rapeseed cake, soybeans, sunflower extraction meal, sugar beet pulp can also be used. Fiber carriers such as fruit pomace, soybean hulls, wheat bran and oils or oilseeds from soybean, rapeseed and sunflower, co-products of food production and minerals and amino acids can be incorporated into the feed mixture to achieve the desired composition.

Thus, administration can be particularly advantageous if the non-therapeutic agent is administered together with a feed for the pigs and the feed is selected from the group consisting of wheat, barley, triticale, soybean extraction meal, rapeseed extraction meal and grain maize.

The energy content of the feed can be chosen broadly. The feed may preferably have a metabolic energy in the range of 10 MJ/kg to 16 MJ/kg. As the energy concentration increases, the amount of feed to be applied is reduced or the growth rate is increased. Advantageous implementations result from compliance with the recommendations made by the Bavarian State Institute for Agriculture (Landesanstalt für Landwirtschaft; LfL) in "Futterberechnung für Schweine" (Feed Calculation for Pigs), 23rd unchanged edition, January 2020. The basis for feed selection and composition is formed by the Weender Futttermittelanalysen (Feed Analysis) and energy estimation equations. Among other things, the above-mentioned document gives supply recommendations and guideline values for gilts breeding, piglet feeding and fattening pig feeding depending on the age of the animals. These recommendations cover a wide range of parameters, such as metabolizable energy, crude protein, lysine and praecaecal digestible lysine, methionine and cysteine, tryptophan and threonine, crude fiber content, calcium, digestible phosphorus and sodium.

In the field of fattening pig feeding, energy concentrations of 13 MJ/kg to 13.6 MJ/kg are advantageous for an optimal fattening result. The effect of guanidinoacetic acid is not dependent on the energy content of the feed and the amount of energy provided as long as no deficiency symptoms occur. Therefore, compliance with the recommendations is beneficial.

Typical analytical values for various types of grains and grain by-products, typical protein feeds, potato and by-products and beets and beet by-products but also of herbage, silages, hay and straw, brewery and dairy products and other food processing by-products, oils and oilseeds as well as additives such as amino acids and minerals are also given. Advantageously, the feed available at the respective location is combined in such a way that the composition of the final feed corresponds to the previously mentioned recommendations.

Guanidinoacetic acid can be administered to animals depending on the feeding system. Generally, guanidinoacetic acid can be administered with the feed or with the water. When administered with the feed, guanidinoacetic acid can be mixed with the finished feed. Advantageous is, however, when the feed mixture is prepared, the guanidinoacetic acid is first added to the basic feed, i.e. the main portion of the feed in terms of quantity, and then the other feed ingredients are added. This has the advantage that no additional mixing time is required. When administered with the water, administration is advantageously carried out as a salt, for example as Na or Ca salt.

In general, administration with the feed is preferable because it provides a more consistent absorption of guanidinoacetic acid by animals. The preferred dosage amount refers to the feed.

Dosing into the water is advantageous when a guanidinoacetic acid-free feed mixture is available and the guanidinoacetic acid must be dosed in a simple manner. However, the water requirements of the animals depending on age and temperature must be taken into account in order to achieve an appropriate dosage.

In the case of dry feeding without water, dry feeding with water and dry feeding on the mash feeder, the dosage can be made both into the water and into the feed. Only in case the respective stable also administers other ingredients with the drinking water, the dosage of guanidinoacetic acid into the water is also appropriate. Otherwise, it has proven easier to administer guanidinoacetic acid in combination with the feed.

In liquid feeding, guanidinoacetic acid can be dosed into the liquid feed and it is distributed homogeneously by simple stirring.

Based on the solid feed amount, a guanidinoacetic acid amount of 0.02 wt. % to 1 wt. %, preferably 0.05 wt. % to 0.2 wt. % can be added to the feed.

The guanidinoacetic acid can be added to the feed in a wide variety of solid preparations or as a solution. Particularly advantageously, the guanidinoacetic acid can be added to the feed in the form of granules, extrudates or as a solution.

If the guanidinoacetic acid is used as a solid or solid preparation, the guanidinoacetic acid may also be applied to a carrier material.

If the guanidinoacetic acid is to be administered as a single dose, guanidinoacetic acid may preferably be administered in a dose of from 4 to 500 mg per day per kg of animal, more preferably from 10 to 200 mg per day per kg of animal, particularly preferably from 20 to 100 mg per day per kg of animal.

The following examples will explain the essence of the invention in more detail.

FIGURE DESCRIPTION

FIG. 1: Drawing of the occupancy of sections 1 and 4
FIG. 2: Drawing of the occupancy of sections 2 and 5
FIG. 3: Drawing of the occupancy of sections 3 and 6
The distance between the boxes with 14.4 m$^2$ and the boxes with 24 m$^2$, which was created by moving the railings, is not shown.

EXAMPLES a) Experiment Description:
A total of 1440 pigs (fattening animals of the Piétrain× Danbred breed) were used.
b) Feeding:
From the 10th day of life until the 27th day of life, the feed was supplemented with Bonimal SB LiquidStart in the form of liquid feed in WEDA Nutrix systems. Ingredients according to the manufacturer: energy (ME) 15.6 MJ, raw protein 21.00%, lysine 1.36%, raw fiber 0.90%, calcium 0.40%, phosphorus 0.60%, additives vitamin A 25,000 I.U., vitamin D3 5,000 I.U., vitamin E 150 mg.

Directly thereafter from the 28th day of life until the 41st day of life it was fed with Bonimal SB Safe spreader 140. Ingredients according to the manufacturer: energy (ME) 14.3 MJ, raw protein 17.50%, lysine 1.14%, raw fiber 3.70%, calcium 0.50%, phosphorus 0.57%, additives vitamin A 16,000 I.U., vitamin D3 2,000 I.U., vitamin E 75 mg.

From the 42nd day of life until the 60th day of life it was fed with Bonimal SK Piglet 138. Ingredients according to the manufacturer: energy (ME) 13.8 MJ, raw protein 17.00%, lysine 1.25%, raw fiber 4.00%, calcium 0.70%, phosphorus 0.53%, additives vitamin A 15,000 I.U., vitamin D3 2,000 I.U., vitamin E 100 mg.

From the 61st day of life until the 90th day of life it was fed with Bonimal SK Piglet 134. Ingredients according to the manufacturer: energy (ME) 13.4 MJ, raw protein 17.00%, lysine 1.20%, raw fiber 3.50%, calcium 0.70%, phosphorus 0.50%, additives vitamin A 15,000 I.U., vitamin D3 2,000 I.U., vitamin E 100 mg.

From the 91st day of life, the experiment started with different dosage of different amounts of guanidinoacetic acid in the feed.

c) Keeping of the Animals:
After a suckling period of 28 days, two-phase piglet breeding was performed until the 60th day of life in a flat deck (0.50 m$^2$ per piglet) in pens of 24 piglets.

The farrowing pens had a size of 5 m$^2$. 1 m$^2$ thereof was heatable with slabs for piglets and 4 m$^2$ with concrete slatted floors with 11 mm slat width and 50 mm tread width. The supplementary feed was provided laterally on two walls in a WEDA Nutrix system.

After 28 days of life, the piglets were transferred to the flat deck with a slat width of 14 mm. The size of each flat deck was 3 m×4 m. Feed with simultaneous access to water was offered in mash feeders. The width of the feeding area was 18 cm. There were 2 bite woods for piglets in each flat deck. Straw was accessible to piglets through a straw basket.

After 60 days of life, 1152 animals were selected for the continuation of the experiment: Here, conspicuously weak animals and animals with easily recognizable injuries to the tail or other body parts were not used.

In the subsequent fattening period, the pigs were kept in 72 pens of 16 animals each on concrete slats without bedding. A drawing of the experimental setup is shown with FIGS. 1 to 3. The slat width was 18 mm with a tread width of 80 mm. Feed was provided ad libitum by means of type RM 05 mash feeders from IBO Stalltechnik GmbH. The feed was supplied via floury feed.

The feeding place width per animal was 33 cm. The following materials were available in all pens: 2 hanging natural bite woods for sows, 2 nibbling balls 5.5 cm in diameter. Straw was accessible through a straw basket. Schurr pig brushes were mounted on two walls.

For each experimental parameter, 6 pens of mixed-sex were housed. For an even distribution, the animals were first divided into 4 main groups 1, 2, 3 and 4 of 288 animals each. Then, from each main group, animals were divided into 3 subgroups A, B and C (SG A, SG B, SG C) of 96 animals each, and from each subgroup, animals were separated into 6 pens. Thus, there were 12 experimental parameters with 6 replications each and 16 animals per replication, corresponding to 1152 animals.

The 72 pens were divided into 6 sections in a stable. All 4 main groups were represented in each section, with a pen size assigned to each main group (see Table 1). The pen sizes of main groups 3 and 4 were realized by removing railings from the standard pen of 12 m². To realize the pen size of main group 2, a part of a 24 m² pen was reduced by a railing. The animals of main groups 1, 2, 3 and 4 were kept without further rehousing with the pen sizes listed in Table 1 until 30 weeks of age.

TABLE 1

Pen size and available space per animal

| Main group | Pen size | Available space per animal |
|---|---|---|
| 1 | 12 m² | 0.75 m²/animal |
| 2 | 14.4 m² | 0.9 m²/animal |
| 3 | 24 m² | 1.5 m²/animal |
| 4 | 36 m² | 2.25 m²/animal |

The available space per animal was chosen based on the National Animal Welfare Label for pigs in Germany. For animals between 50 and 110 kg, the following regulations apply: Minimum standard: 0.75 m²/animal; level 1: 0.9 m²/animal; level 2: 1.1 m²/animal; level 3: 1.5 m²/animal (of which 0.5 m² is outdoor space).

Accordingly, main group 1 corresponds to the statutory German minimum standard, main group 2 corresponds to level 1 of the National Animal Welfare Label in terms of space requirements, and main group 3 corresponds to level 3 of the National Animal Welfare Label in terms of space requirements but in confinement without outdoor space. The animals in main group 4 were offered significantly more space than the highest level of the National Animal Welfare Label so far.

Feeding from 91 days of life was performed in 2 phases, which were identical across all 4 main groups.

Phase I: from the 91st day of life until the 120th day of life
Phase II: from the 121st day of life For subgroups B and C, guanidinoacetic acid was added to the feed in amounts of 0.04 wt. % and 0.12 wt. %, respectively, relative to the solid feed.

The mixing was carried out in a HIMEL compact mixer FM with a capacity of 560 kg, in which the feed was introduced and guanidinoacetic acid was added as a powder and mixed for 15 min at the highest performance level.

The calculated contents of energy, raw protein and amino acids per kg of the feed used (880 g TM (dry weight)) are shown in Table 2.

TABLE 2

Calculated contents and metabolic energy of the feed

| | | Phase I 91st-120th day of life | Phase II > 120th day of life |
|---|---|---|---|
| Energy conversion (ME) | MJ | 13.2 | 13.0 |
| Raw protein | g | 155 | 140 |
| Lysine | g | 9.1 | 7.6 |
| Methionine + Cystine | g | 5.9 | 5.4 |
| Threonine | g | 6.2 | 5.5 |
| Thryptophan | g | 1.9 | 1.7 |
| Isoleucine | g | 5.2 | 4.8 |
| Valine | g | 6.4 | 6.0 |

Each stable section is crossed by three pipe chain conveyors, which can fill each automatic feeder. By opening or closing the sliders accordingly, it is possible to preset via which pipe chain a feeder is filled. In this way, up to three different feeds can be fed in one section.

Table 3 shows the experimental regime (see also FIGS. 1 to 3).

TABLE 3

Experimental regime

| Main group | Available space [m²/animal] | No GAA SG A | 0.04 wt. % GAA SG B | 0.12 wt. % GAA SG C |
|---|---|---|---|---|
| 1 | 0.75 | A1 | B1 | C1 |
| 2 | 0.9 | A2 | B2 | C2 |
| 3 | 1.5 | A3 | B3 | C3 |
| 4 | 2.25 | A4 | B4 | C4 |

Scoring was performed when the stand was replaced using the classification shown in Table 4.

TABLE 4

Score

| | |
|---|---|
| 1 | Without abnormalities |
| 2 | Dry bite marks, not bleeding |
| 3 | Bloody bite marks, moderate inflammation |
| 4 | (Partial) loss, high-grade inflammation, large bleeding wounds |

A maximum of 2 failures occurred per experimental regime during the fattening phase. Here, the score was evaluated at the time of the failure.

Results

Essential for an evaluation of the stand is the ratio of uninjured or only slightly injured animals to moderately and severely injured animals. Since dry, non-bloody bite marks result from a playful non-aggressive act, animals with score 2 were added to the non-injured animals. Harmful to animal welfare is considered to occur at score 3 and above, i.e., bloody bite marks, resulting from aggressive acts that are no longer playful. Therefore, for an evaluation, the numbers for scores 3 and 4 were added and the percentage of these animals relative to the total number of the respective experimental group was evaluated.

TABLE 5

Overall result: Number of animals with the corresponding scores for the respective test parameters

| Experiment | Score 1 | Score 2 | Score 3 | Score 4 | Total score 3 + 4 |
|---|---|---|---|---|---|
| A1 | 39 | 42 | 12 | 3 | 15 |
| A2 | 41 | 41 | 11 | 3 | 14 |
| A3 | 43 | 42 | 9 | 2 | 11 |
| A4 | 46 | 43 | 6 | 1 | 7 |
| B1 | 41 | 41 | 10 | 4 | 14 |
| B2 | 50 | 36 | 8 | 2 | 10 |
| B3 | 54 | 36 | 5 | 1 | 6 |
| B4 | 55 | 35 | 6 | 0 | 6 |
| C1 | 40 | 43 | 10 | 3 | 13 |
| C2 | 52 | 36 | 6 | 2 | 8 |
| C3 | 56 | 35 | 4 | 1 | 5 |
| C4 | 55 | 35 | 5 | 1 | 6 |

A) Consideration of the Influence of the Available Space Per Animal

In each case, 288 animals were kept at the respective spaces, namely 0.75 m$^2$/animal, 0.9 m$^2$/animal, 1.5 m$^2$/animal and 2.25 m$^2$/animal. Here, all animals were included in the evaluation regardless of whether they were given no guanidinoacetic acid or 0.04 wt. % guanidinoacetic acid or 0.12 wt. % guanidinoacetic acid in the feed.

TABLE 6

Result available space

| Available space [m$^2$/animal] | Experiments | Number of animals score 3 or 4 | Injured animals [%] |
|---|---|---|---|
| 0.75 | A1 + B1 + C1 | 42 | 14.6 |
| 0.9 | A2 + B2 + C2 | 33 | 11.1 |
| 1.5 | A3 + B3 + C3 | 22 | 7.6 |
| 2.25 | A4 + B4 + C4 | 19 | 6.6 |

As can be seen from Table 6 above, as the amount of space increases, the number and percentage of injured animals decreases. Without being bound by theory, it can be assumed that when there is too little freedom of movement per animal, their aggression is encouraged, resulting in the tail biting effect. Furthermore, a large spatial proximity creates significantly more opportunities for animal-animal interactions.

B) Consideration of the Influence of Supplementation with Guanidinoacetic Acid without Taking into Account the Available Space Per Animal:

In each case 384 animals were kept at the different supplementation rates with guanidinoacetic acid, namely without supplementation, at 0.04 wt. % supplementation and at 0.12 wt. % supplementation. Here, all animals were included in the evaluation, regardless of the space available per animal in each case.

TABLE 7

Result supplementation guanidinoacetic acid

| GAA in feed [wt. %] | Experiments | Number of animals score 3 or 4 | Injured animals [%] |
|---|---|---|---|
| 0 | A1 + A2 + A3 + A4 | 47 | 12.2 |
| 0.04 | B1 + B2 + B3 + B4 | 36 | 9.4 |
| 0.12 | C1 + C2 + C3 + C4 | 32 | 8.3 |

As shown in Table 7 above, the number and percentage of injured animals decreases with guanidinoacetic acid supplementation. Even at a low level of supplementation, namely with 0.04 wt. % guanidinoacetic acid, a significant reduction occurs from 12.2% injured animals without supplementation to 9.4% injured animals when supplemented with 0.04 wt. % guanidinoacetic acid. When the supplemented amount of guanidinoacetic acid is increased from 0.04 wt. % to 0.12 wt. %, the percentage of injured animals is further reduced from 9.4% to 8.3%.

C) Consideration of the Influence of Supplementation with Guanidinoacetic Acid Considering the Available Space Per Animal:

In each case, 96 animals were kept at different supplementation rates with guanidinoacetic acid, namely without supplementation, at 0.04 wt. % supplementation, and at 0.12 wt. % supplementation, and at different amounts of space per animal, namely 0.75 m$^2$/animal, 0.9 m$^2$/animal, 1.5 m$^2$/animal, and 2.25 m$^2$/animal.

TABLE 8

Overall assessment of guanidinoacetic acid supplementation

| GAA in feed [wt. %] | Available space [m$^2$/animal] | Experiment | Injured animals [%] |
|---|---|---|---|
| 0 | 0.75 | A1 | 15.6 |
| 0.04 | 0.75 | B1 | 14.6 |
| 0.12 | 0.75 | C1 | 13.5 |
| 0 | 0.9 | A2 | 14.6 |
| 0.04 | 0.9 | B2 | 10.4 |
| 0.12 | 0.9 | C2 | 8.3 |
| 0 | 1.5 | A3 | 11.5 |
| 0.04 | 1.5 | B3 | 6.3 |
| 0.12 | 1.5 | C3 | 5.2 |
| 0 | 2.25 | A4 | 7.3 |
| 0.04 | 2.25 | B4 | 6.3 |
| 0.12 | 2.25 | C4 | 6.3 |

In the experiments where only 0.75 m$^2$/animal was available to the animals, namely A1, B1, and C1, supplementation with guanidinoacetic acid only slightly decreased the percentage of injured animals, from 15.6% (without supplementation) to 14.6% (supplementation with 0.04 wt. % guanidinoacetic acid) and to 13.5% (supplementation with 0.12 wt. % guanidinoacetic acid).

In the experiments where 0.9 m$^2$/animal was available to the animals, namely A2, B2 and C2, supplementation with guanidinoacetic acid significantly reduced the percentage of injured animals, from 14.6% (without supplementation) to 10.4% (supplementation with 0.04 wt. % guanidinoacetic acid) and to 8.3% (supplementation with 0.12 wt. % guanidinoacetic acid). This almost halved the number of injured animals. The effect was particularly large between the experiments without the addition of guanidinoacetic acid with 14.6% injured animals and supplementation with 0.04 wt. % guanidinoacetic acid with 10.4% injured animals.

In the experiments where 1.5 m²/animal was available to the animals, namely A3, B3 and C3, supplementation with guanidinoacetic acid reduced the percentage of injured animals only slightly, from 11.5% (without supplementation) to 6.3% (supplementation with 0.04 wt. % guanidinoacetic acid) and to 5.2% (supplementation with 0.12 wt. % guanidinoacetic acid). The number of injured animals was more than halved in this series of experiments. Again, the greatest decrease was observed between the experiments without the addition of guanidinoacetic acid with 11.5% injured animals and supplementation with 0.04 wt. % guanidinoacetic acid with 6.3% injured animals.

In the experiments where 2.25 m²/animal was available to the animals, namely A4, B4 and C4, supplementation with guanidinoacetic acid reduced the percentage of injured animals only slightly, from 7.3% (without supplementation) to 6.3% (supplementation with 0.04 wt. % and 0.12 wt. % guanidinoacetic acid, respectively). On the one hand, the effect of supplementation was only slight, and on the other hand, the increase in the supplemented amount of guanidinoacetic acid from 0.04 wt. % to 0.12 wt. % did not result in any reduction in the number of injured animals.

In summary, it is concluded that the addition of guanidinoacetic acid to pig feed decreases the number of animals injured at the tail. This effect is particularly evident in those animals that had an available space of 0.9 m²/animal and 1.5 m²/animal, respectively. However, the positive influence of guanidinoacetic acid supplementation on the number of tail-injured animals is also evident in the case of an available space of 0.75 m²/animal and 2.25 m²/animal.

Without being bound by theory, it is assumed that at a space requirement of 0.75 m²/animal there is such a high stress level that supplementation can hardly reduce this stress level, since the available space is below the natural space requirement. With a space requirement of 2.25 m²/animal, the distance between animals is so great that animal-animal interactions are less likely to occur. An attacker's aggression can reduce before the animal acts out its aggression, and the attacked animal has more space available to escape.

Supplementation with guanidinoacetic acid consequently reduces aggressive behavior and behavioral disorders of pigs, such as tail biting, and consequently the resulting injuries and finally the economic losses.

The invention claimed is:
1. A method for treating caudophagia in pigs, wherein guanidinoacetic acid is administered to the pigs as an agent for reducing aggressiveness, wherein the agent is administered during breeding or fattening of the pigs, wherein the pigs are provided with space in the range of 0.75 to 2.25 m2/animal.
2. The method according to claim 1, wherein the agent is administered from the 60th day of life of the pigs.
3. Use or The method according to claim 1, wherein the agent is administered together with a feed for the pigs.
4. The method according to claim 3, wherein the feed is selected from the group consisting of wheat, barley, triticale, soybean extraction meal, rapeseed extraction meal and grain maize.
5. The method according to claim 1, wherein the feed has a metabolic energy in the range of 10 to 16 MJ/kg feed.
6. The method according to claim 1, wherein the guanidinoacetic acid is administered in a dose of 4 to 500 mg per day per kg of animal.
7. The method according to claim 1, wherein the guanidinoacetic acid is administered in an amount of from 0.02 to 1 wt. % based on the feed.
8. The method according to claim 1, wherein the guanidinoacetic acid is added to the feed in the form of a granulate, extrudate or solution.
9. The method according to claim 1, wherein the guanidinoacetic acid is applied to a carrier material.

\* \* \* \* \*